United States Patent [19]

DeZeeuw

[11] Patent Number: 4,628,033
[45] Date of Patent: Dec. 9, 1986

[54] **NOVEL HOST STRAIN FOR TRANSFORMATION OF *YARROWIA LIPOLYTICA***

[75] Inventor: John R. DeZeeuw, Stonington, Conn.

[73] Assignee: Pfizer Inc., New York, N.Y.

[21] Appl. No.: 539,363

[22] Filed: Oct. 6, 1983

[51] Int. Cl.[4] .................... C12N 15/00; C12N 1/00; C12N 1/16
[52] U.S. Cl. .................... 435/255; 435/172.1; 435/172.3; 435/317; 935/28; 935/69; 935/29
[58] Field of Search .................. 435/172.1, 172.3, 254, 435/255, 317, 911, 921, 923; 935/66, 69

[56] References Cited

U.S. PATENT DOCUMENTS 4,155,811  5/1979  Nubel et al. .................... 435/923
4,407,953 10/1983  DeZeeuw et al. ................ 435/923

OTHER PUBLICATIONS

Uchiyama, H. et al., European J. Biochem vol. 125(3) pp. 523–527, 1982, Chem. Abst. 97:159259r.

*Primary Examiner*—Thomas G. Wiseman
*Assistant Examiner*—Jayme A. Huleatt
*Attorney, Agent, or Firm*—Charles J. Knuth; Albert E. Frost; Peter C. Richardson

[57] ABSTRACT

A *Yarrowia lipolytia* strain (PC-30827) ATCC 20688 which is utilized as a suitable host for cloning. The strain is a double auxotroph and requires medium supplemented with leucine and uracil for growth.

3 Claims, 5 Drawing Figures

NOVEL HOST STRAIN FOR TRANSFORMATION OF YARROWIA LIPOLYTICA

BACKGROUND OF THE INVENTION

1. Field of the Invention

This invention relates to a process for the transformation of *Yarrowia lipolytica* to improve its utilization for industrial purposes; to vectors and subclones thereof useful therefor, especially to vectors which replicate autonomously in *Escherichia coli* and integrate but do not replicate autonomously in *Yarrowia lipolytica;* to transformants of *E. coli* and *Y. lipolytica* containing said vectors and to their use for producing proteins.

2. Description of the Prior Art

Major emphasis in molecular cloning has been directed to prokaryotes, particularly *E. coli*, and more recently *Bacillus subtilis*, as host organisms. *E. coli*, despite its extensive use as host organism for the cloning and expression of heterologous DNA, is known to pose certain problems, such as the possibility of contamination of the protein produced with a toxic substance and the possible need to destroy the cells to recover the protein. This latter problem may not only aggravate the contamination problem, but may also tend to degrade the protein product and to complicate the procedures for recovering the protein.

In view of the cited difficulties, particularly toxin production, *B. subtilis* has been turned to as an alternative host organism since it does not produce toxins. However, as host organism, *B. subtilis* is subject to certain limitations; instability of transformed strains resulting in loss of heterologous DNA, and the frequent reduction in the ability of the entering DNA to coexist with the host DNA.

In recognition of the above-mentioned difficulties with prokaryotes as host organisms, attention shifted to eukaryotes, and specifically yeasts, as host organisms. Yeasts are of industrial importance, are non-toxic and can be grown to very high densities. Some species are well analyzed genetically and some species can secrete proteins.

The first transformation of a yeast, *Saccharomyces cerevisiae*, was reported by Hinnen et al., Proc. Natl. Acad. Sci., 75, 1929-1933 (1978) who demonstrated that a cloned segment of yeast DNA encoding the LEU2 locus could transform a nonreverting leu2− mutant of yeast to a LEU+ phenotype. This transformation was shown to result from integration into the chromosome of the plasmid containing the LEU2 segment of DNA. The integration involved recombination between homologous segments of DNA.

Hinnen et al. in "Overproduction of Microbial Products", edited by Krumphanzl et al., Academic Press, N.Y., Ch. 30, 1982, present a review of yeast transformation procedures. Typical of such procedures is that described by Ratzkin et al., Proc. Natl. Acad. Sci. 74, 487-491 (1977) in their cloning of yeast (*Saccharomyces cerevisiae*) LEU2 by complementation of an *E. coli* leuB mutation.

Sjostak et al., Plasmid 2, 536-554 (1979) describe the construction of plasmids containing the LEU2 gene of yeast and fragments of rDNA and the integration of the plasmids into the rDNA locus following yeast transformation. The basic thrust of their investigation involved the integration of a genetic marker, the LEU2 gene, inserted into the rDNA locus, as a genetic marker for mapping the rDNA. One of the reported plasmids, pSZ20, containing the BglII-B fragment of rDNA and the SalI-XhoI LEU2 fragment, is identified as a useful vector for cloning fragments of yeast DNA in yeast.

Orr-Weaver et al., Proc. Natl. Acad. Sci., 78, 6354-6358 (1981) demonstrated high frequency integration of linear plasmids derived from pBR322, all of which are nonreplicating in yeast and transform only by integration, in *Saccharomyces cerevisiae* when the plasmids are cut within DNA sequences homologous to the yeast chromosome.

*Yarrowia lipolytica*, an industrially important species of yeast, is used to produce citric acid and single cell protein. It can also be used to produce erythritol, mannitol and isopropylmalic acid. It is of special interest and value because of its ability to secrete proteins (alkaline protease, acid protease and RNAse) into its growth medium, thus permitting recovery of said proteins without the need of disrupting the producing cells. However, *Y. lipolytica* suffers from certain inherent deficiencies, such as its limited spectrum of utilizable carbon sources. The overall value of *Y. lipolytica* could be increased by eliminating such deficiency as, for example, by introducing correcting DNA from another species.

SUMMARY OF THE INVENTION

Pending application Ser. No. 634,505 of L. S. Davidow et al. describes a process for the transformation of *Y. lipolytica* by introducing therein DNA comprising a fragment of *Y. lipolytica* DNA or, alternatively and preferably, a vector containing or including a fragment of *Y. lipolytica* DNA, said DNA or vector being detectable in said *Y. lipolytica*, vectors useful therefor, and microbial transformants comprising said vectors. In general in this transformation process, the *Y. lipolytica* DNA fragment contains a selectable marker which functions in *Y. lipolytica*, especially in *Y. lipolytica* having a mutation in the gene corresponding to said selectable marker. Of particular interest and value to this invention is the use of a *Y. lipolytica* DNA fragment having the LEU2 gene (codes for the enzyme beta-isopropylmalate dehydrogenase, EC1.1.1.85) or the HIS1 gene (codes for the enzyme ATP phosphoribosyltransferase, EC2.4.2.17), and *Y. lipolytica* strains having a leu2− mutation or a his 1− mutation, respectively.

In general, for purposes of this invention, the production of useful vectors is based upon preparation of hybrid vectors; i.e., vectors which function physiologically in a microorganism, desirably a bacterium, and preferably *E. coli*, and also in *Y. lipolytica*. Such vectors comprise microbial DNA and fragments of chromosomal DNA of *Y. lipolytica* which fragments contain a selectable genetic marker; that is, a gene which functions in and is detectable in *Y. lipolytica*. The thus constructed vectors interact with homologous chromosomal sequences in *Y. lipolytica* becoming integrated into a chromosome thereof, thus achieving transformation.

Integration is achieved with circular, linear and gapped-linear forms of said vectors. Linear and gapped-linear vectors integrate with higher efficiency than do circular vectors. The vectors desirably, therefore, have a unique restriction site; i.e., a site not present in the original microbial DNA vector or elsewhere in the *Y. lipolytica* fragment component of the vector. Linearization of the vector at such a site generates double stranded DNA having highly recombinogenic ends capable of transforming *Y. lipolytica* by integration at homologous chromosomal sequences. As Orr-Weaver et al. (loc. cit.) have shown in *S. cerevisiae*, gapped-linear plasmids are also capable of integration. Such plasmids are prepared by making two restriction enzyme cuts within the *Y. lipolytica* chromosomal DNA segment of the vector. In the case of pLD25 described below, the presence of two BglII sites conveniently allows preparation of gapped-linear plasmids.

The value of the vectors of this invention is based upon the presence therein of a selectable genetic marker, detectable in and functional in *Y. lipolytica*, hence, a detectable marker. Suitable markers are the following *Y. lipolytica* genes: LEU2 and HIS1, but as those skilled in the art will recognize any *Y. lipolytica* gene which affords a selection can be used. The LEU2 gene, all or a part thereof, is especially valuable. Said gene or part thereof is obtained from *Y. lipolytica* by a partial digest of the chromosomal DNA of *Y. lipolytica* by a suitable restriction endonuclease, for example, Sau3A. Said vectors or subclones thereof permit creation of *Y. lipolytica* cloning vectors by inserting therein random segments of DNA by known methodology. The resulting vectors are then used to transform *Y. lipolytica* strains having a mutation in the gene corresponding to the selectable marker. The transforming DNA having such a *Y. lipolytica* marker can provide selective growth advantage to the recipient or correct for an auxotrophic mutation in the recipient.

It is generally preferred to employ a *Y. lipolytica* DNA fragment which contains the entire leu2$^-$ gene since said fragment permits preparation of a vector which functions physiologically in both *E. coli* and *Y. lipolytica*. However, use of a *Y. lipolytica* DNA fragment having the entire leu2 gene is not necessary for successful conduct of the process of this invention. It is only necessary to employ a DNA fragment that includes the wild-type sequence to correct the mutation in the recipient. Said fragment, while not functional in *E. coli* is detectable in *Y. lipolytica*.

Also valuable for the preparation of vectors useful in this invention are fragments of *Y. lipolytica* DNA obtained by a complete BamHl digest of *Y. lipolytica* chromosomal DNA and which include the HIS1 gene thereof. Said fragments, when ligated with linearized, e.g. using BamHl, YEp24 (Botstein et al., Gene 8, 17-24, 1979) afford hybrid vectors carrying the HIS1 gene.

Using the vectors described herein, particularly those identified as pLD21, pLD23, pLD24 and pLD25, random segments of *Y. lipolytica* can be inserted therein by the "shotgun" technique. The resulting vectors can be used to transform various mutants and transformants selected by standard methods. For example, a pLD25 derived shotgun library can transform a leu2$^-$ ura3$^-$ double mutant using the unique KpnI site for integration, and transformants selected for growth on a medium lacking leucine and uracil. The resulting cloned URA3 gene in any transformants selected can then be subcloned away from the LEU2 gene and used as an effective *Y. lipolytica* vector.

In general a bacterial, e.g. *E. coli*, plasmid replication origin and a selective genetic marker for said bacterium are combined by known methodology with all or part of a *Y. lipolytica* gene which can be selected for, and detected, in *Y. lipolytica*. The *E. coli* cloning system is especially useful since it readily affords large amounts (bulk) of plasmid DNA by growth and amplification in *E. coli*; and permits construction of vectors and gene libraries in *E. coli*.

The herein described plasmids are useful as vectors in recombinant DNA methodology. Various genes can be inserted into them and the resulting plasmids transformed into a suitable host microorganism, e.g. yeasts such as *S. cerevisiae* and *Y. lipolytica* which, upon culturing under appropriate conditions, produces the desired product. Plasmid pLD25 which contains the LEU2 gene from *Y. lipolytica* can be selected in and detected in a *Y. lipolytica* recipient. It can thus be used to enable the creation of *Y. lipolytica* cloning vectors.

Additionally, the herein described plasmids afford means for improving fermentation characteristics of microorganisms, especially of *Y. lipolytica*, to improve the industrial usefulness by overcoming inherent deficiencies therein. For example, genes coding for utilization of various carbon sources can be introduced into them and the resulting plasmid transformed into a suitable host such as *Y. lipolytica* to modify the nutritional characteristics of said host, thus broadening the spectrum of utilizable carbon sources of *Y. lipolytica*.

The vectors, e.g. plasmids or cosmids, needed for this purpose can be constructed by techniques familiar to those skilled in the art of recombinant DNA technology. The *Y. lipolytica* DNA sequence coding for a particular periplasmic enzyme is isolated by known methods and inserted into, for example, pLD25 or a derivative thereof. A desired structural gene, for example, the maltase gene, can appropriately be fused into the DNA sequence for a periplasmic enzyme and the resulting plasmid transformed into *Y. lipolytica* and integrated into one of *Y. lipolytica*'s chromosomes by the process of this invention. The thus-produced transformant upon culturing is capable of hydrolyzing maltose into glucose, a desirable property not possessed by the parent.

Plasmid pLD25 replicates autonomously in *E. coli* and integrates but does not replicate autonomously in *Y. lipolytica*. It is obtained by inserting into *E. coli* replicating plasmid pBR322 a *Y. lipolytica* DNA fragment desirably endowed with two distinctive properties; first, the presence of a structural gene which functions physiologically in *Y. lipolytica* and preferably also in *E. coli* and which is detectable in *Y. lipolytica*; second, possession of a unique restriction site (i.e., not present in the original *E. coli* plasmid or elsewhere in the *Y. lipolytica* host fragment) in a region flanking the DNA sequence which is introduced into the *Y. lipolytica* host strain for the purpose of correcting defects in the structural gene of said host. In order to achieve high frequency of transformation possession of a unique restriction site is essential.

Plasmids pLD21 and pLD23 described below, each of which carries the HIS1 gene of *Y. lipolytica* are obtained by inserting into YEp24 and pBR322, respectively, a fragment obtained by the complete BamHl digestion of chromosomal DNA of *Y. lipolytica*.

Plasmid pLD25 contains a fragment of *Y. lipolytica* DNA that complements *E. coli* leuB$^-$ mutations, and plasmids pLD21 and pLD23 a fragment that complements *E. coli* hisG$^-$ mutations.

REFERENCE TO THE DRAWINGS

FIG. 1. Sau3A partial digest gene library of *Y. lipolytica* in pBR322. This agarose gel shows that the library (marked LIB) contains some pBR322 supercoiled plasmid without insert DNA migrating just above the 2.3 kb lambda-HindIII standard (marked STD), while the remainder of the molecules contain diverse (4–10 kb) size-fractionated inserts of *Y. lipolytica* DNA migrating as a nearly continuous smear above the 4.3 kb standard. The lane in between contains an uncut plasmid (pLD21) and shows two discrete bands.

FIG. 2. Southern hybridization of EcoRI digested *Y. lipolytica* bulk DNA and pLD25 probed with radioactive pLD25. The three internal bands labelled b, c, and d of pLD25 show homology to identically sized pieces of total *Y. lipolytica* DNA. Two additional, fainter bands (labelled 1 and 2) in the *Y. lipolytica* lane probably have homology to the small *Y. lipolytica* portions of plasmid bands a and e. The lane marked "STD" contains lambda-HindIII size standards. The lane marked "P" contains approximately 2 ng of EcoRI digested pLD25. The lane marked "Y1" contains approximately 1 microgram of total *Y. lipolytica* DNA. In a similar Southern experiment using pBR322 as a probe, only bands a and e from pLD25 hybridized.

FIG. 3. Restriction Map of pLD25. A partial restriction map based on single and some double restriction digests is shown. Sites enclosed in brackets have not been ordered with respect to each other. All sizes indicated are approximations based on agarose gel observations. The thin line represents pBR322 DNA (in the standard format with the EcoRI site at 12 o'clock) and the thick line represents insert DNA from *Y. lipolytica*. The insert has 3 EcoRV (RV), 8 AvaI (A—but only one has been mapped), 1 SphI (Sp), 1 KpnI (K), 2 SalI (S), 4 EcoRI (RI), 2 XhoI (X) and 2 close-together BglII (B) sites. The insert lacks HindIII, ClaI, BamHI and NruI sites. A 2.3 kb subclone with EcoRI ends, marked leu2 is functional in *E. coli* in only 1 orientation in the EcoRI site of pBR322.

FIG. 4. Southern hybridization of HindIII digested bulk DNA from *Y. lipolytica* transformants with radioactive pBR322 probe. HindIII digests of total DNA isolated from four different transformants and the parent strain were run on an agarose gel, blotted and probed with labelled pBR322. *Y. lipolytica* transformant #6 was randomly chosen from a culture transformed with intact, circular pLD25. Transformants 11, 12 and 15 were from a culture transformed with KpnI-linearized pLD25. All *Y. lipolytica* transformants gave two bands of hybridization, a stronger one (1) of greater than 23 kb length and a fainter one (2) the same size as the 9.3 kb lambda-HindIII standard. The lane marked PC contained parental (PC30827) DNA with no significant hybridization to the probe.

FIG. 5. Restriction Digests of pLD23 and pLD24. This agarose gel contains lambda-HindIII size standards in the outer left lane, and (a) EcoRI, (b) BamHI, (c) no enzyme treatments of pLD23 (complements *E. coli* hisG mutants) and pLD24 (fails to complement) respectively. Each lane b contains two close-together BamHI bands: the larger corresponding to pBR322 and the slightly smaller band (approximately 4 kb) representing the *Y. lipolytica* BamHI insert. The EcoRI digests show that the *Y. lipolytica* piece is in opposite orientations in the two plasmids.

DETAILED DESCRIPTION OF THE INVENTION

The Plasmid

Figure 1:
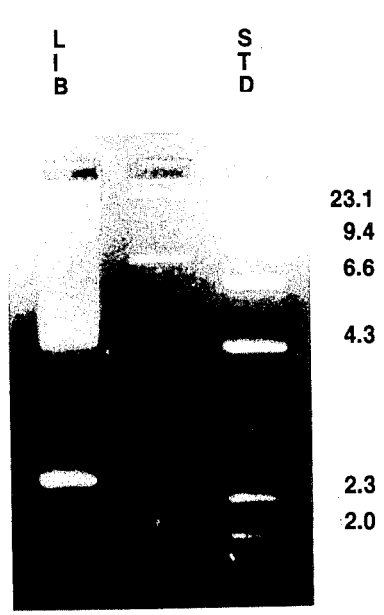

Plasmid pLD25 contains selectable genetic markers for *E. coli* and *Y. lipolytica* and is derived from the *E. coli* replicating plasmid pBR322, a multicopy plasmid. It was constructed by inserting into the BamHI site of pBR322, ca. 6.6 kb fragment obtained by a partial digestion of *Y. lipolytica* chromosomal DNA by Sau3A.

The Microorganisms

The starting microorganisms are a strain of *E. coli* and a strain of *Y. lipolytica*, which strains are identified in the culture collection of Pfizer Inc. as *E. coli* JC-355 [Clark et al., Molec. Gen. Genet. 105, 1 (1969) obtained as strain No. 869 from the *E. coli* Genetic Stock Center, Yale University], and *Y. lipolytica* PC-30827, respectively. A further microorganism, *E. coli* MC1061, utilized in the production of a gene library of *Y. lipolytica* in vector pBR322 is described by Casadaban et al., J. Mol. Biol. 138, 179–207 (1980). It is particularly useful for this purpose because of its ability to achieve high frequency of transformation. Other microorganisms can be used in place of said *E. coli* MC1061. Representative of suitable microorganisms are strains of *E. coli* which are restriction minus, such as *E. coli* HB101 (NRRLB-11371) and which can be made competent for transformation.

*Y. lipolytica* PC-30827 has been deposited under the terms of the Budapest Treaty in the American Type Culture Collection, Rockville, Md., a recognized depository affording permanence of the deposits and ready accessibility thereto by the public if a patent is granted on this application. It was given the designation *Yarrowia lipolytica* ATCC 20688. The deposit is available during pendency of this application to one determined by the Commissioner of the United States Patent and Trademark Office to be entitled thereto under 37 CFR 1.114 and 35 USC 122, and in accordance with foreign patent laws in countries wherein counterparts of this application, or its progeny, are filed. All restrictions on the availability to the public of the microorganisms deposited will be irrevocably removed upon granting of the patent.

The taxonomic study of *Y. lipolytica* ATCC 20688 was conducted by Dr. L. H. Huang who provided the description given below. The media and methods used are those recommended by J. Lodder in "The Yeasts", second edition, N. Holland Publishing Co., Amsterdam, 1970.

CBS 599, the type culture for the species *Candida lipolytica*, [also known as *Saccharomycopsis lipolytica*; now classified as *Yarrowia lipolytica* (Wickerham et al.) by van der Walt and von Arx, Antonie van Leeuwenhoek 46, 517–521, 1980], was run for comparison.

Since strain PC-30827 requires leucine and uracil (J. R. DeZeeuw), both leucine ethyl ester and uracil at concentrations of 149 mg/L and 20 mg/L, respectively, were added to the following defined media: basal medium for assimilation of carbon compounds, the broth for assimilation of potassium nitrate, the vitamin-free broth for growth and the broth for testing the effect of vitamins on growth stimulation. Leucine ethyl ester as compared to leucine is slowly utilized as a carbon source. The other media were organic in nature and should support growth without the supplements. In strain CBS-599 the above-mentioned defined media with and without the supplements were also used.

As shown in the descriptions which follow, the cultures shared most of the cultural and morphological characteristics in common. A few differences were noticed. For example, the streak culture of strain CBS-599 on glucose-yeast extract-peptone agar was slightly roughened or slightly wrinkled, that of strain PC-30827 finely wrinkled. Strain PC-30827 showed poor growth on corn meal agar and produced less true mycelium when compared with strain CBS-599.

In strain CBS-599, the results in which the defined media were supplemented with leucine ethyl ester and uracil were the same as those without the supplements except that citric acid was utilized without the supplements but not in the medium with the supplements. This indicates that the supplements were not used as either carbon or nitrogen sources; thus their addition to the defined media for strain PC-30827 is acceptable.

Compared with strain CBS-599, strain PC-30827 showed no to weak rather than good growth on succinic acid, D-glucitol, and glycerol; no rather than weak growth on vitamin-free medium and salicin; no to weak rather than good growth on thiamine for growth stimulation. Strain PC-30827 failed to grow on L-sorbose whereas the reverse was true for strain CBS-599.

The several differences in biochemical tests between strain PC-30827 and CBS-599 were quantitative in nature. The mutant strain PC-30827 shared most of the biochemical tests in common with the type culture CBS-599. When the results were used in a key to the species of Candida proposed by van Uden and Buckley in *The Yeasts*, Ed. J. Lodder, 1970, each of the two strains was keyed to *Candida lipolytica*—the imperfect state of *Yarrowia lipolytica*.

Strain CBS-599

Growth on glucose-yeast extract-peptone water:

After 3 days at 28° C. the cells are ovoid, elongated ovoid to elongated, with one to three buds. The ovoid cells measure 5–16×3–7 m; the elongated cells measure up to 30 m long. Pseudomycelium present; a pellicle present; sediment.

Growth on glucose-yeast extract-peptone agar:

After one month at 28° C. the culture is cream, raised, slightly roughened or slightly wrinkled, with a dull or moist surface.

Dalmau plate cultures on corn meal agar:

Growth moderate, off-white. Pseudomycelium and true, septate mycelium are present. Single, paired or three ovoid blastospores are formed terminally or pleurally on the hyphae or pseudohyphae, sometimes in a verticillate fashion.

Fermentation:

Negative on glucose, galactose, sucrose, maltose, trehalose and lactose.

Assimilation of carbon compounds:

Basal medium (basal medium plus leucine ethyl ester and uracil)

| Glucose | +(+) | Soluble | −(−) | Ribitol | −(−) |
|---|---|---|---|---|---|
| Galactose | −(−) | starch | | Galactitol | −(−) |
| L-Sorbose | +(+) | D-Xylose | −(−) | D-Mannitol | +(+) |
| Sucrose | −(−) | L-Arabinose | −(−) | D-Glucitol | +(+) |
| Maltose | −(−) | D-Arabinose | −(−) | Salicin | − to weak |
| Cellobiose | −(−) | D-Ribose | weak (weak) | | (− to weak) |
| Trehalose | −(−) | L-Rhamnose | −(−) | DL-Lactic acid | weak (+) |
| Lactose | −(−) | Ethanol | +(+) | | |
| Mellibiose | −(−) | Glycerol | +(+) | alpha-methyl- | −(−) |
| Raffinose | −(−) | Erythritol | +(+) | D-Glucoside | |
| Melezitose | −(−) | Inositol | −(−) | Succinic acid | +(+) |
| Citric acid | +(−) | | | | |

Assimilation of potassium nitrate (with or without leucine ethyl ester and uracil):
Negative.

Growth in vitamin-free medium (with or without leucine ethyl ester and uracil):
Weak growth.

Vitamin stimulating growth:
Thiamine in broths with or without leucine ethyl ester and uracil stimulates growth.

Sodium chloride tolerance: 11%–12%.

Maximum temperature of growth:
Between 37° C. and 45° C.

Strain PC-30827

Growth in glucose-yeast extract-peptone water:

After 3 days at 28° C. the cells are ovoid, elongated ovoid, elongated, rarely elliptical, with one to three buds. The ovoid cells measure 5–14×3–6 μm; the elongated cells measure up to 25 μm long. Pseudomycelium present; a pellicle present; sediment.

Growth on glucose-yeast extract-peptone agar:

After one month at 28° C. the streak culture is cream, raised, finely wrinkled, with a dull surface.

Dalmau plate cultures on corn meal agar:

Growth poor, off-white. Pseudomycelium is present, sparse and short. True, septate mycelium is rarely present. Single or paried ovoid to globose blastospores are formed terminally or pleurally, sometimes in groups.

Fermentation:

Negative on glucose, galactose, sucrose, maltose, trehalose and lactose.

Assimilation of carbon compounds: (basal medium plus leucine ethyl ester and uracil)

| Glucose | weak | Soluble starch | − | Ribitol | − |
|---|---|---|---|---|---|
| Galactose | − | | | Galactitol | − |
| L-Sorbose | − | D-Xylose | − | D-Mannitol | + |
| Sucrose | − | L-Arabinose | − | D-Glucitol | − to weak |
| Maltose | − | D-Arabinose | − | Salicin | − |
| Cellobiose | − | D-Ribose | weak | DL-Lactic acid | weak |
| Trehalose | − | L-Rhamnose | − | alpha-Methyl- | − |
| Lactose | − | Ethanol | weak | D-Glucoside | |
| Melibiose | − | Glycerol | − to weak | Succinic acid | − to weak |
| Raffinose | − | Erythritol | + | Citric acid | − |
| Melezitose | − | | | Inositol | − |

Assimilation of potassium nitrate (plus leucine ethyl ester and uracil):
Negative.

Growth in vitamin-free medium (plus leucine ethyl ester and uracil):
Negative.

Vitamin stimulating growth:
Thiamine in broth with leucine ethyl ester and uracil stimulates weak or no growth.

Sodium chloride tolerance:
11%–12%.

Maximum temperature of growth:
Between 37° C. and 45° C.

*Y. lipolytica* PC-30827 contains the rarely reverting mutation leu2-35. The *Y. lipolytica* LEU2 gene codes for the enzyme beta-isopropylmalate dehydrogenase (EC1.1.1.85) and is coded for by the leuB gene in *E. coli* and the LEU2 gene in *S. cerevisiae*.

Insertion of pLD25 into each of *E. coli* JC-355 and *Y. lipolytica* ATCC 20688 gave transformants comprising pLD25 in *E. coli* JC-355 and in *Y. lipolytica* ATCC 20688, respectively. They are identified in the culture collection of Pfizer Inc. as F.D. 27534 and F.D. 27533, respectively. Each of the transformants has been deposited in the ATCC under the conditions of access thereto as set forth above, and been assigned the accession number ATCC 39464 and ATCC 20687, respectively.

Chromosomal DNA from *Y. lipolytica* strain NRRL Y-1094, a wild-type strain (i.e., a strain customarily used by those skilled in the art for microbiological processes) was obtained by the method of Hereford et al., Cell, 18, 1261–1271 (1979).

The novel plasmid pLD25 of this invention was constructed by ligation of linearized pBR322 with a partial Sau3A digest of *Y. lipolytica* chromosomal DNA by means of T4 ligase. The pBR322 was isolated by centrifugation in CsCl-ethidium bromide gradients to separate covalently closed supercoiled pBR322 from bacterial DNA. The pBR322 was linearized by cleavage within the tetracycline resistance gene (Tc®) by digestion with the restriction endonuclease BamHI resulting in a linear fragment having cohesive (sticky) ends and leaving ampicillin resistance (Amp®) as the phenotypic trait. Gel (agarose) electrophoresis of the vector showed it to be substantially free of bacterial DNA. The linearized pBR322 thus-produced is then desirably treated with alkaline phosphatase to prevent subsequent self-ligation; i.e., recircularization and dimer formation of the vector DNA.

The second component of pLD25 is obtained by subjecting the chromosomal DNA of *Y. lipolytica* strain NRRL Y-1094, a wild-type strain, to partial digestion with restriction endonuclease Sau3A which generates cohesive ended, nearly random fragments complimentary to those of the BamHI cleavage of pBR322. DNA in the range of 4–10 kb, harvested from agarose gels, was purified by known procedures prior to ligation with BamHI-cut, alkaline phosphatase treated vector pBR322.

The size of the DNA fragments is not critical to the process of this invention. The critical aspect as regards said DNA fragments is that they contain all or a part of the detectable marker, e.g. the LEU2 gene. Additionally, they must contain cohesive ends complimentary to those generated by the restriction endonuclease cleavage of the *E. coli* plasmid, in this case, pBR322.

The vector DNA and the partial Sau3A digest of *Y. lipolytica* chromosomal DNA are ligated by means of T4 ligase in the presence of adenosine triphosphate (ATP) as cofactor.

The ligation mixture is first transformed into *E. coli* MC 1061 (Casdaban et al., J. Mol. Biol. 138, 179–207, 1980), a strain of *E. coli* which gives a very high transformation frequency and is hsdR⁻ hsdM+, thus affording a *Y. lipolytica* gene library in said *E. coli*. The total potentially different ampicillin-resistant transformants of *E. coli* MC 1061 were grown together on ampicillin plus L agar plates and harvested. The harvested culture was grown in one liter of ampicillin containing medium. The mixed plasmids were isolated by standard methodology to produce a gene library. A sample of said library was transformed into *E. coli* JC-355. Transformants were selected on the basis of ampicillin resistance. These transformants were then replica plated to synthetic media lacking leucine. Alternatively, the transformation mixture could be directly plated on synthetic media lacking leucine and containing ampicillin. Several transformants thus selected were leucine prototrophic. The plasmid in said transformants is isolated by standard methods and referred to as pLD25.

Plasmid minipreparations made from the rare leucine prototrophic transformants and analyzed by digestion with HindIII and SalI are found to contain the expected 3.7 kb fragment from pBR322 and 2 large fragments indicating an insert size of approximately 6.6 kb. Additionally, a small fragment (from the SalI site of pBR322 to the nearer SalI site of the insert see FIG. 3) was found. Comparison of Southern blot hybridizations (Southern, J. Mol. Biol. 98, 503–517, 1975) of plasmid pLD25 with hybridizations of EcoRI digested chromosomal DNA of *Y. lipolytica* showed the 3 fragments internal to the cloned insert to be identical in the chromosomal DNA.

Transformants of *Y. lipolytica* with intact pLD25 and with KpnI-cut pLD25 were tested to determine whether they contain integrated or independently replicating pLD25 (the LEU2-containing plasmid). Chromosomal DNA was prepared from the leucine prototrophic transformants and the parent *Y. lipolytica* ATCC 20688. The DNA samples were cleaved with HindIII, run on 0.5% agarose gel, and analyzed by the Southern blot technique using radioactive pBR322 to measure the presence of plasmid pLD25 in the samples. No homology between the parent *Y. lipolytica* strain and the probe was observed. Since there is one HindIII site in pLD25 (within the pBR322 segment), and none in the *Y. lipolytica* segment, one band of pLD25 size (approximately 10.8 kb) would be seen if pLD25 was replicating independently in the transformants. The absence of such a band leads to the conclusion that the transformants are all integrants. Circular, linearized and gapped-linearized plasmids can transform *Y. lipolytica* by recombination with homologous chromosomal sequences. However, the transformants frequency was much higher in the KpnI-cut plasmid-treated cells than in the intact plasmid-treated cells further indicating that integrative transformation as described by Orr-Weaver et al. (Proc. Natl. Acad. Sci., 78, 6354–6358, 1981) occurred. The Southern blots mentioned above show that the structure of the integrated transformants derived from linear molecules is identical to that of transformants derived from circular molecules (i.e. plasmids).

EXPERIMENTAL

Materials and Methods:

The DNA restriction enzymes BamHI, SalI and HindIII, and Sau3A were obtained from New England Biolabs (NEB) as was T4 DNA ligase and *E. coli* polymerase I. They were used according to the conditions for their use described by the respective manufacturers. SalI was also obtained from Bethesda Research Laboratories (BRL), as was the bacterial alkaline phosphatase, KpnI and XhoI. The bacterial alkaline phosphatase was used at approximately 100 units per microgram of linearized plasmid DNA at 65° C. in BamHI assay buffer for two hours. Restriction digests were analyzed by electrophoresis in submerged 0.8% agarose gels using Tris-Borate-EDTA buffer (Maniatis et al., "Molecular Cloning", Cold Spring Harbor Laboratory, N.Y., 1982).

Media:

E. coli rich medium was L broth containing, per liter, 10 g Bacto-tryptone, 5 g Bacto-yeast extract, and 5 g NaCl, adjusted to pH 7.5. E. coli minimal medium was 56 salts with 0.33% dextrose (Low, J. Bacteriol. 113, 798-812, 1973). Amino acids or bases were supplemented to 50 ug/ml where needed. Bacteria were grown at 37° C.

Yeast rich medium was YPD, containing 1% Bacto-yeast extract, 2% Bacto-Peptone, and 2% dextrose. Yeast minimal medium, SD, contained 0.67% Bacto-yeast nitrogen base without amino acids and 2% dextrose. Synthetic complete medium contained 870 mg/l of powdered stock supplements made by grinding the following together in a mortar and pestle: 2 g each of adenine sulfate, uracil, tryptophan, histidine-HCl, arginine-HCl and methionine, 3 g tyrosine, 6 g leucine, 5 g phenylalanine, 20 g threonine, 3 g lysine. For nutritional testing or selection, the appropriate ingredient was left out of complete medium. Y. lipolytica was grown at 28° C.

Isolation of Y. lipolytica Chromosomal DNA: a. Cloning Quality DNA.

The wild type strain NRRL Y-1094 was grown at 28° C. to $1-2 \times 10^8$ cells per ml in $4 \times 300$ ml of YPD in shaking Fernbach flasks, following inoculation with 15 microliters from a fresh stationary phase culture. All of the following manipulations of the cells were performed at 28° C. or room temperature. The cells were harvested by centrifugation, washed in 50 ml 1M NaCl, and spun down again. Then, a 15 minute "pre-spheroplasting" incubation in 50 ml of 0.2M tris(hydroxymethyl)aminomethane-HCl (Tris-HCl) pH 8.5, 0.02M ethylenediaminetetracetic acid (EDTA), 1M NaCl, and 0.1M 2-mercaptoethanol was followed by centrifugal harvesting. The cell pellet was resuspended in 40 ml of 1M NaCl containing 1 mg per ml zymolyase 5000 (from Kirin Breweries, Japan) and incubated for 45 minutes. At this time greater than 90% of the cells were converted to spheroplasts as detected microscopically by cell lysis upon dilution into water.

The spheroplasts were spun down and resuspended in 4 tubes in a total of 16 ml 1M NaCl. Forty ml of lysis buffer [50 mM Tris pH 6.8, 100 mM NaCl, 100 mM EDTA, 0.5% sodium dodecylsulfate (SDS)] containing 0.1 mg/ml proteinase K was added and the lysate incubated at 37° for 1.5 hours. The lysate was extracted with an equal volume of phenol:chloroform (1:1). Following centrifugation at 9000 rpm to separate the phases, the aqueous phase was again extracted with phenol-chloroform. The final aqueous phase was combined with two volumes of ethanol to produce large precipitates of DNA. The liquid was poured off and the pellet rinsed with 70% and 100% ethanol before vacuum drying. The dried pellet was redissolved in 8 ml TE (10 mM Tris-HCl pH 8, 1 mM EDTA) at 65° C. followed by RNAse digestion with 300 microliters of RNAse A (1 mg/ml, boiled 5 minutes) for 1 hour at 37° C. The material was extracted twice with phenol-chloroform and ethanol precipitated as before. The final precipitate was rinsed with ether before vacuum drying.

The DNA pellet was redissolved in TE as before and 2 ml $100 \times$ TE was added followed by water to 29.04 g. The solution was added to 37.67 g of CsCl, transferred into centrifuge tubes, and spun for 17 hours at 40,000 rpm at 15° C. in a Beckman L8-70 ultracentrifuge using a VTi 50 rotor. The gradient was harvested by dripping fractions containing approximately 1.25 ml from the bottom of the tube following puncture with a needle. The fractions were assayed for DNA by running samples on an agarose gel containing 0.5 mg/ml ethidium bromide, and fractions 16, 17, and 18 (out of 26) were saved. These DNA-containing fractions were pooled, dialyzed against four changes of $1 \times$ TE and ethanol precipitated. The DNA was redissolved in 0.6 ml $1 \times$ TE and the preparation was estimated, by absorbance at 260 nm, to contain 129 micrograms of DNA.

b. DNA for Southern Blots.

We found that the SDS spheroplast lysis and potassium acetate treatment from the S. cerevisiae mini-prep method (compiled in Sherman et al., "Methods in Yeast Genetics", Cold Spring Harbor Laboratory, N.Y., 1981) was convenient for obtaining Y. lipolytica DNA.

Preparation of Plasmid DNA.

Bacterial plasmid DNA was prepared by the rapid boiling method of Holmes et al., Anal. Biochem. 114, 193-197 (1981). Subsequent centrifugation in CsCl-ethidium bromide gradients were performed only for large scale preparations. DNA preparations were stored at 4° C. in sterile TE buffer.

E. coli Transformation.

The $CaCl_2$ method of Dagert et al., Gene 6, 23-28 (1979) was used. Both overnight $CaCl_2$-treated and briefly treated cells were used in transformations.

Southern Blot Experiments.

DNA transferred to nitrocellulose (Southern 1975) was hybridized to $^{32}$P-labelled "nick translated" probes in $6 \times$ SCP buffer ($20 \times$ SCP stock contains 2.0M NaCl, 0.6M $Na_2HPO_4$, and 0.2M EDTA pH 6.2), 1% sacrosyl, with 40 ug/ml denatured calf thymus or E. coli DNA. The nick translation method of Maniatis et al. (loc. cit.) was used with E. coli polymerase I.

Preparation of Sau3A Partial Digests of Y. lipolytica DNA.

Approximately 15 micrograms of this DNA was partially digested with the restriction enzyme Sau3A (New England Biolabs) in each of four tubes using 0.05, 0.1, 0.2 and 0.4 enzyme units per microgram of DNA for 0.5 hour at 37° C. following the suppliers protocol. The reactions were stopped by heating at 65° C. for 10 minutes then loaded onto 0.8% preparative agarose gels. DNA in the size range of 4 to 10 kilobases (compared to HindIII-cut lambda size standards from Bethesda Research Labs) was harvested from the gels, electroeluted, purified on DE52 columns (Yang et al., Methods in Enzymology, 68, 176, 1979) and ethanol precipitated before ligation with BamHI-cut, alkaline phosphatase-treated, vector pBR322.

Construction of a Gene Library of Y. lipolytica in Vector pBR322.

The ligation mix containing approximately 1 ug of DNA was used to transform E. coli strain MC1061 (Casadaban et al., J. Mol. Biol. 138, 179-207, 1980) to create a Y. lipolytica gene library. The transformation mixture gave approximately $1.4 \times 10^4$ colonies on 10 mg/ml ampicillin plus L agar plates. Fifty colonies were placed on a single plate and replica plated to test resistance to 5 mg/ml tetracycline. Forty-four (88%) were sensitive indicating they most likely contained an insert in the BamHI site to interrupt the tet ® gene of pBR322. Mini-scale plasmid preparations from 18 randomly chosen amp ® colonies were examined by restriction enzyme digestion with HindIII and SalI double digests and BamHI digests. Ten of the plasmids had inserts, averaging approximately 7 kilobases in size.

Forty-eight ampicillin plates containing approximately $1.4 \times 10^4$ E. coli transformant colonies were replica plated to LB plus 10 ug/ml ampicillin. The replicas were washed with 5 ml 0.85% NaCl each. The pooled cells were pelleted by centrifugation and resuspended in 11 ml LB and 2.5 ml 80% glycerol. Two cultures with 1 L of LB and 10 ug/ml ampicillin Fernbach flasks were set up with 4 ml of the pooled bacteria each, and the remaining bacteria were stored at $-70°$ C. The cultures were used to prepare the plasmid DNA that was designated as our *Y. lipolytica* gene library of Sau3A partial digest fragments in pBR322.

Screening the Gene Library in *E. coli* Mutants.

Several *E. coli* strains mutant for different genetic markers were transformed with the gene library. In order to obtain genetic complementation, two major factors are necessary: (1), the corresponding *Y. lipolytica* gene must be contained intact on at least one of the plasmids in our library; and (2), the *Y. lipolytica* gene must function to a sufficient extent in *E. coli* cells. The library was screened both by direct selection for each marker on the appropriate medium and also by initial selection for ampicillin resistance followed by replica plating onto selective medium. For each genetic marker examined, at least $10^5$ transformants were examined. Strain JC355 was used to successfully clone the LEU2 gene.

Any *E. coli* colonies that grew on selective media were further examined by a "re-transformation" test. For this test, plasmid was prepared from a 5 ml culture of the strain that grew on selective media. The plasmid mini prep was then used to transform that parent, mutant *E. coli* strain. The presence of many ampicillin-resistant transformants but few or no colonies on selective media, led to the conclusion the original colony did not contain the desired *Y. lipolytica* gene and most likely grew because of mutation to prototrophy. If all of the ampicillin-resistant colonies also grew on selective media for the gene being tested, it was concluded that the plasmid obtained from the original colony contained an insert that complemented the *E. coli* mutation. A total of 7 leucine-independent transformants of JC355 (leuB6) that contained the identical insert into pBR322 were found. Plasmid mini-preparations from two of these colonies gave 100% (37/37 and 31/31) ampicillin-resistant leucine prototrophic transformants in the re-transformation test. The plasmid was designated pLD25.

Verification that the *E. coli* leuB6-Complementing DNA came from *Y. lipolytica*.

Figure 2:
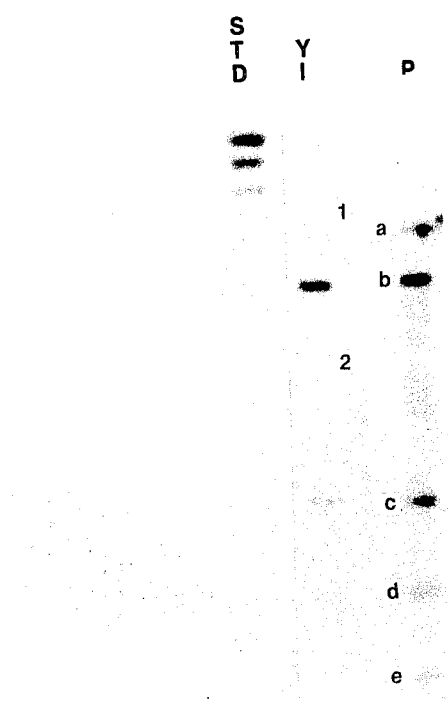

To verify that the insert DNA from pLD25 came from *Y. lipolytica*, a Southern (1975) blot experiment was performed. A new preparation of *Y. lipolytica* total DNA was made, omitting the final CsCl gradient step. The EcoRI digestion pattern of the *Y. lipolytica* DNA revealed identity with three bands internal to the insert in pLD25 (FIG. 2).

Further Characterization of the Insert in pLD25.

Figure 3:
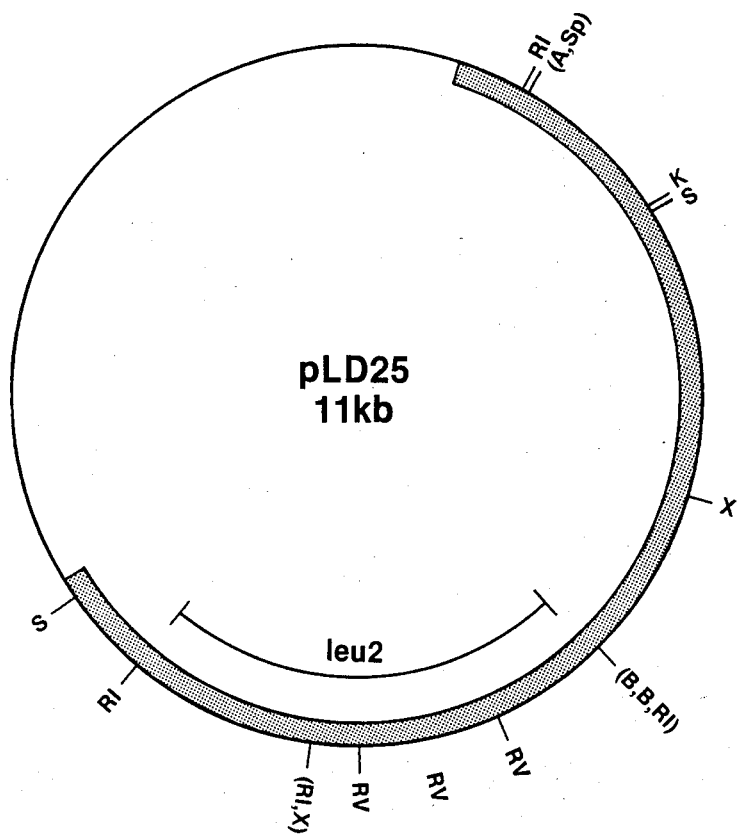

A partial restriction map of pLD25 was derived using several common enzymes (FIG. 3). The total amount of *Y. lipolytica* DNA contained in the plasmid was estimated at approximately 6.6 kb.

Transformation Protocol.

A modification of the lithium acetate method (Ito et al., J. Bacteriol. 153, 163–168, 1983) with the sonicated carrier DNA addition used for *S. cerevisiae* transformation was adapted for *Y. lipolytica* transformation. Late log phase cultures $3-10 \times 10^7$ cells/ml usually gave more transformants than log phase ($1 \times 10^7$ cells/ml) cultures. Fifty ml YPD cultures were pelleted and then resuspended in 10 ml of 10 mM Tris, 1 mM EDTA ph 7.5. They were repelleted and resuspended in 2–3 volumes of the above buffer plus 0.1M lithium acetate and mixed gently on a New Brunswick roller drum at 28° C. for 1 hour. The Li-treated cells were separated into multiple tranformation tubes containing between 0.1 and 1.0 ml of cells, 1 ug of transforming plasmid and 50 ug sonicated heterologous carrier DNA (the size range appeared to be 0.5–9 kb on an agarose gel). The transformation tubes were left at 28° C. for 30 minutes and then 7 volumes of PEG reagent (40% polyethylene glycol, 0.1M LiAc, 10 mM Tris, 1 mM EDTA pH 7.5—filter sterilized) was added. After an additional 1 hr at 28° C., the heat pulse (usually 37° C. for 5 minutes) was used. The cells were finally spun down, resuspended in water, and plated on appropriate media.

Transformation of a *Y. lipolytica* leu2 Mutant with pLD25.

*Y. lipolytica* strain PC-30827 (MATA leu2-35 ura3-11) constructed by J. R. DeZeeuw was used as a recipient for the LEU2 gene cloned in pLD25. It was found that cultures in later stages of growth gave more transformants than early log phase cells. This finding held true even when approximately equal numbers of early vs. late log phase cells were treated with DNA and plated on leucine-deficient plates. Plasmids that had been linearized by either a cut at a unique restriction site or by leaving a small gap (BglII-cut) in the *Y. lipolytica* DNA gave many more transformants than intact pLD25 or plasmid linearized by cutting at the HindIII restriction site in pBR322. These latter results are similar to the integrative transformation system in *S. cerevisiae* developed by Orr-Weaver et al., loc. cit. The addition of sonicated *E. coli* DNA to the pLD25 used in transformation gave more transformants than when either large molecular weight or no carrier DNA was added. Minor variations in the duration and temperature of the heat shock following incubation of the cells with DNA and polyethylene glycol appears to have only a small effect on the yield of transformants.

Stability of the Transformants.

A colony of the transformant comprising pLD25 in *Y. lipolytica* ATCC 20687, designated herein as DL10, was streaked out on a YPD plate for single colonies following growth non-selectively on a YPD plate. The resulting YPD culture plate was replicated onto leucine-deficient synthetic medium. All of the approximately 50 well-separated colonies were leucine independent, demonstrating stability of the transformants.

Southern Blot to Detect Integration of pLD25.

Figure 4:
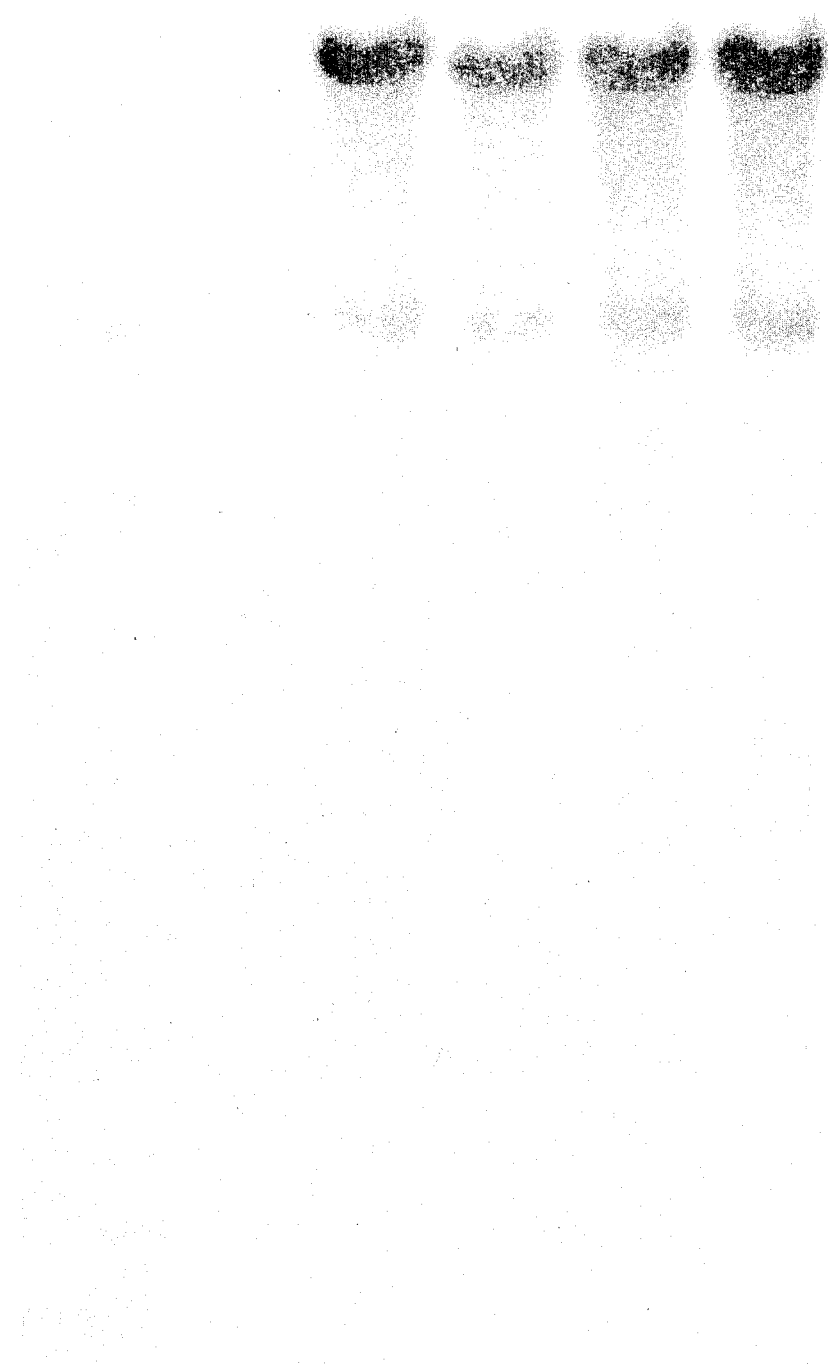

The *Y. lipolytica* transformants were stable and the transformation frequency was greatly increased by linearization of the donor plasmid DNA. This indicated the transformants resulted from integration of the plasmid into chromosomal DNA at the site homologous to the ends of the donor DNA as found in the *S. cerevisiae* system by Orr-Weaver et al., loc. cit. A Southern blot experiment (FIG. 4) of HindIII digests of *Y. lipolytica* DNA showed the same two bands of homology to pBR322 in transformants resulting from either intact or linearized plasmid. The observation that one band was larger than the 23 kilobase lambda size standard is evidence of integration of the plasmid into chromosomal DNA.

Cloning of *Y. lipolytica* HIS1 Gene

Gene Library Construction.

The vector YEp24 (Botstein et al., Gene 8, 17-24, 1979) was digested with BamHI and treated with alkaline phosphatase as described previously for pBR322. The insert DNA used in the ligation reaction was a complete BamHI digest of Y. lipolytica chromosomal DNA obtained from Y. lipolytica NRRL Y-1094 as described above. The chromosomal DNA digest was not size-fractionated before ligation, only phenol extracted. A total of approximately 27,000 ampicillin-resistant transformant colonies of E. coli strain MC 1061 were obtained using the ligation products. The plasmid DNA obtained from cultures of these pooled transformant colonies was designated as the library of BamHI fragments of Y. lipolytica in YEp24. The insert frequency was estimated as 95 percent (19/20 transformants were tetracycline-sensitive) and the average insert size was 4.2 kb.

Isolation of the HIS1 Gene.

The BamHI library was used to transform many different E. coli auxotrophs in an attempt to find a Y. lipolytica gene that would complement a mutant E. coli gene. Two transformant colonies of the E. coli hisG1 mutant AT2535 (obtained as #4517 E. coli Genetic Stock Center, Yale University) were isolated on synthetic medium lacking histidine and containing ampicillin. Both colonies contained the same plasmid pLD21, which consisted of an insert of approximately 4 kb into the vector. The retransformation test was positive with 419/419 ampicillin-resistant transformants of AT2535 with pLD21 scored as histidine-independent by replica plating. A Southern hybridization experiment showed that the BamHI insert in pLD21 as well as the two insert fragments generated by a BamHI plus EcoRI double digest, co-migrated with fragments of Y. lipolytica chromosomal DNA that had been similarly cut.

To test if other alleles of hisG could be complemented by pLD21, E. coli strain NK5526 (E. coli Genetic Stock Center #6416) which contains a Tn10 insertion into the HISG gene, was transformed with the plasmid. All ampicillin-resistant transformant colonies were capable of slow growth following replica plating to media without histidine as would be expected from the polarity effect of Tn10 on the downstream genes in the histidine operon. Direct selection for the transformants on defined media lacking histidine and containing ampicillin was not possible, presumably because of the strong polarity effect. Since the Y. lipolytica DNA insertion in pLD21 was capable of complementing hisG mutations in E. coli, we concluded that it contained the Y. lipolytica HIS1 gene in a form that functioned in E. coli.

The Effect of Orientation on Expression.

Figure 5:
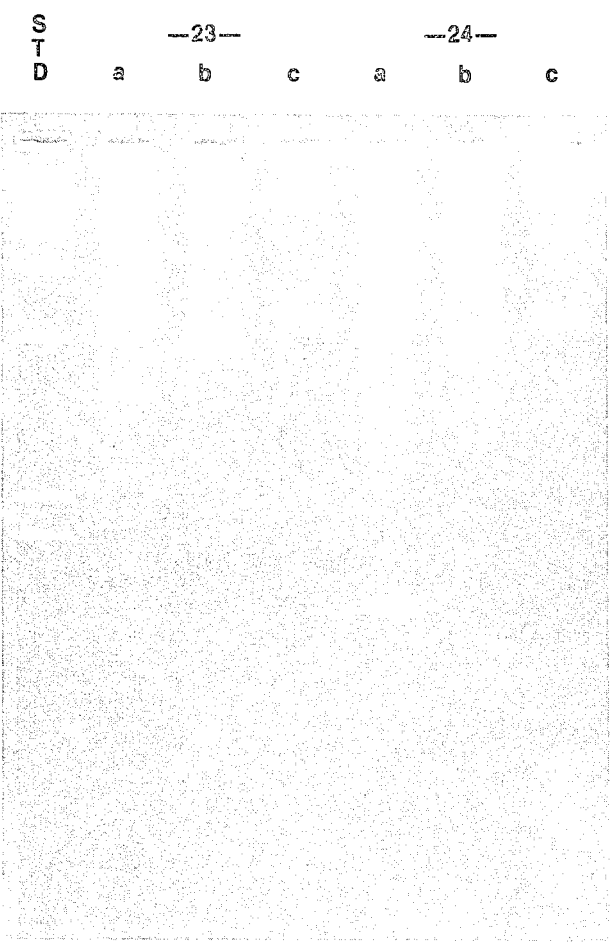

To test if the Y. lipolytica DNA insert was functioning independently of the vector YEp24, the BamHI piece was subcloned into pBR322. Inserts in both orientations were determined by the EcoRI digest pattern (FIG. 5). Plasmid pLD23, the plasmid with the EcoRI site of the insert further from the EcoRI site of pBR322, complemented the two hisG E. coli mutants used previously, whereas pLD24, the other orientation failed to complement the mutations. Thus, a sequence on the plasmid is needed for efficient expression of the Y. lipolytica HIS1 gene in this E. coli system. It is believed the tet ® promoter of pBR322 is the necessary component.

Transformation with Extended Segments of Chromosomal DNA.

The approximately 5.4 kb long SalI piece of Y. lipolytica DNA containing the LEU2 gene (gel purified from a plasmid digest) was found to be capable of transforming the Y. lipolytica leu2 mutant recipient to prototrophy at a high frequency (greater than 1000 transformants per microgram). This integration event represents a different kind of recombination from transformation with a linearized plasmid. It affords the opportunity of inserting a desired sequence within a region of Y. lipolytica DNA and integrating the desired sequence without also integrating the bacterial vector into the host.

I claim:

1. A biologically pure culture of Yarrowia lipolytica having the identifying characteristics of ATCC 20688.

2. A biologically pure culture of Yarrowia lipolytica ATCC 20688.

3. The culture of claim 2 in freeze dried form.